United States Patent [19]
Brodbeck

[11] Patent Number: 5,447,435
[45] Date of Patent: Sep. 5, 1995

[54] DEVICE FOR THE RECONSTRUCTION OF TEETH

[76] Inventor: Urs Brodbeck, Sempacherstrasse 27, Ch-8032 Zürich, Switzerland

[21] Appl. No.: 257,481

[22] Filed: Jun. 6, 1994

Related U.S. Application Data

[63] Continuation of Ser. No. 946,636, Sep. 18, 1992, abandoned.

[30] Foreign Application Priority Data

Sep. 18, 1991 [CH] Switzerland ............. 02757/91

[51] Int. Cl.$^6$ .................................................. A61C 8/00
[52] U.S. Cl. ....................................... 433/173; 433/172
[58] Field of Search ............... 433/172, 173, 174, 175, 433/176, 215, 201.1, 199.1

[56] References Cited

U.S. PATENT DOCUMENTS

| | | | |
|---|---|---|---|
| 2,721,387 | 10/1955 | Ashuckian | 433/173 |
| 4,259,072 | 3/1981 | Hirabayashi et al. | 433/173 |
| 4,575,340 | 3/1986 | Lustig | 433/173 |
| 4,746,293 | 5/1988 | Lundgren et al. | 433/173 |
| 4,824,372 | 4/1989 | Jorneus et al. | 433/174 |
| 4,854,872 | 8/1989 | Detsch | 433/174 X |
| 4,872,839 | 10/1989 | Brajnovic | 433/173 |
| 4,955,811 | 9/1990 | Lazzara et al. | 433/173 |
| 5,040,983 | 8/1991 | Biron | 433/173 |
| 5,064,373 | 11/1991 | Staubli et al. | 433/173 |
| 5,071,345 | 12/1991 | Rosen | 433/173 X |
| 5,082,442 | 1/1992 | Rosen | 433/173 X |
| 5,106,300 | 4/1992 | Voitik | 433/173 |
| 5,125,839 | 6/1992 | Ingber et al. | 433/173 X |
| 5,135,395 | 8/1992 | Marlin | 433/174 |
| 5,152,687 | 10/1992 | Amino | 433/173 |

FOREIGN PATENT DOCUMENTS

| | | |
|---|---|---|
| 0320024 | 6/1989 | European Pat. Off. . |
| 0477644 | 4/1992 | European Pat. Off. . |
| 2157139 | 5/1972 | Germany . |
| 3224112 | 2/1984 | Germany . |
| 3825601 | 3/1989 | Germany . |
| 4127839 | 3/1992 | Germany . |
| 2213065 | 8/1989 | United Kingdom . |
| 1570720 | 6/1990 | U.S.S.R. . |

OTHER PUBLICATIONS

Literature: Singer, Hans: Der vorgefertigte Wurzelstift mit individuellem Kernaufbau. In: Die Quintessenz (1965).

Primary Examiner—Nicholas D. Lucchesi
Attorney, Agent, or Firm—Burns, Doane, Swecker & Mathis

[57] ABSTRACT

In a device for the reconstruction of missing or lost teeth, an implant, which ends in the gingival region, is biologically anchored in a jawbone. The implant itself comprises an implant body anchored in the jawbone and an implant head on the gingival aspect, acting as the anchoring site for an abutment, which in turn forms the reception site for the tooth being reconstructed. The abutment represents the retention shape of the tooth being reconstructed.

13 Claims, 4 Drawing Sheets

5,447,435

DEVICE FOR THE RECONSTRUCTION OF TEETH

This application is a continuation of application Ser. No. 07/946,636, filed Sep. 18, 1992 now abandoned.

FIELD OF THE INVENTION

The present invention relates to devices and processes for the reconstruction of missing or lost teeth.

BACKGROUND OF THE INVENTION

In the reconstruction of missing or lost teeth according to present-day technique, an implant is secured to the patient's jawbone. This implant, which preferably is made of titanium or a titanium alloy, comprises an anchor pin anchored in the bone and a receiving funnel on the gingival aspect, whose end is located in the gingival region below the gingival contour. An abutment, which preferably consists of titanium or a titanium alloy, is advantageously attached to the implant head via a detachable connection and represents the actual receiving core for a reconstruction of a tooth or a bridging anchor. Towards the gingival opening, this abutment has a thickening, which represents the actual receiving site for the reconstructed tooth crown. The end of the abutment directed towards the oral cavity is firmly joined to the gingival opening of the tooth crown, preferably with the aid of a bonding or screwing procedure. However, the tooth configurations of each individual assume different manifestations with regard to shape, geometric extent and position within the dental arch, for which reason difficult adjustments are regularly required in the region of the thickening at the gingival aspect of the abutment if one wishes to deviate more or less, with the reconstructed tooth crown, from the predetermined perpendicular indicated by the abutment anchored in the implant head, or to change the root dimensions predetermined by the implant post. The commercially available range of shapes allows little scope for matching to the desired tooth/not shape and position of the neighboring teeth. This difficult adjustment consists, for example, in making an individual modification to the thickening at the gingival aspect of the abutment, as recipient site for the reconstructed tooth crown, in order to effect a corresponding correction in the attitude and shape of the tooth being reconstructed. Clearly, such on-the-spot reworking poses considerable visual and technical demands, and this, with anything less than optimal performance of the correction, has an immediately negative effect on the quality of the work. A further important disadvantage of this concept is evident in that, with the slightest recession of the gingiva, the abutment will be exposed. This will be evident in the form of a black linear arch above the gingival boundary, which always leads to considerable impairment of the cosmetic appearance, something which frequently results in the existing concept being unacceptable. Also, as intimated above, the last-named concept does not permit any satisfactory correction of the gingival emergence profile.

SUMMARY OF THE INVENTION

The object of the invention is to provide a remedy for the defects of prior tooth implants and procedures, and to provide a process by which teeth to be reconstructed can be configured in an optimal fashion.

The essential advantages of the invention are that the basis of every reconstruction is provided by an individual or standardized abutment, which is processed to a retention shape with regard to the final shaping of the tooth to be reconstructed, this shaping being carried out preferably by machining with the aid of a copy-milling operation, preceded by a preliminary modeling of the individual form in wax or synthetic material; a more expensive manual working is not excluded. Obviously, the abutment can also be shaped without cutting, for example using a sinter technique.

A further essential advantage of the invention consists in the fact that there is the possibility of preparing the whole tooth reconstruction, i.e., abutment and tooth crown, in one piece so that the abutment represents the actual reconstruction.

The following possibilities are available in principle:
A. The abutment comes ready for use with a retention shape.

The latter can be prepared ready-made or individually:
   a) with a metal core; sheathing of ceramic, or a synthetic or of a composite material;
   b) completely of metal;
   c) completely of ceramic, of a synthetic or of a composite material.
B. The abutment represents the actual individually prepared reconstruction of the tooth:
   a) with a metal core; sheathing of ceramic, or a synthetic or of a composite material;
   b) completely of metal;
   c) completely of ceramic, of a synthetic or of a composite material.
C. The abutment is fashioned as a telescope and used for providing detachable prostheses.

In a preferred embodiment having a metal core, the sheathing has the form of an integral or quasi-integral jacket around the metal core. In the case of the quasi-integral embodiment, the jacket, composed of one of the above-mentioned substances, reaches deep down into the anchoring region of the abutment in such a way that, even if there is extensive gingival recession, no metallic exposure of the metallic core results, thereby maximizing the acceptance of the subject of the invention.

Since the retention shape corresponds exactly to the reconstruction with regard to shaping, any subsequent corrective adjustment of the abutment is rendered superfluous. The very delicate alignment of the tooth being reconstructed, to conform to dentition, is completely dispensed with, which in turn maximizes assurance of quality.

The above-mentioned embodiments are naturally also valid with regard to the alignment of the abutment as a complete tooth reconstruction.

BRIEF DESCRIPTION OF THE DRAWINGS

Preferred embodiments of the invention are illustrated in the drawings. All the elements which are not required for the immediate understanding of the invention have been omitted. In the drawings, the same elements are provided with the same reference numerals in the various figures, and in which.

DETAILED DESCRIPTION

Figure 1:
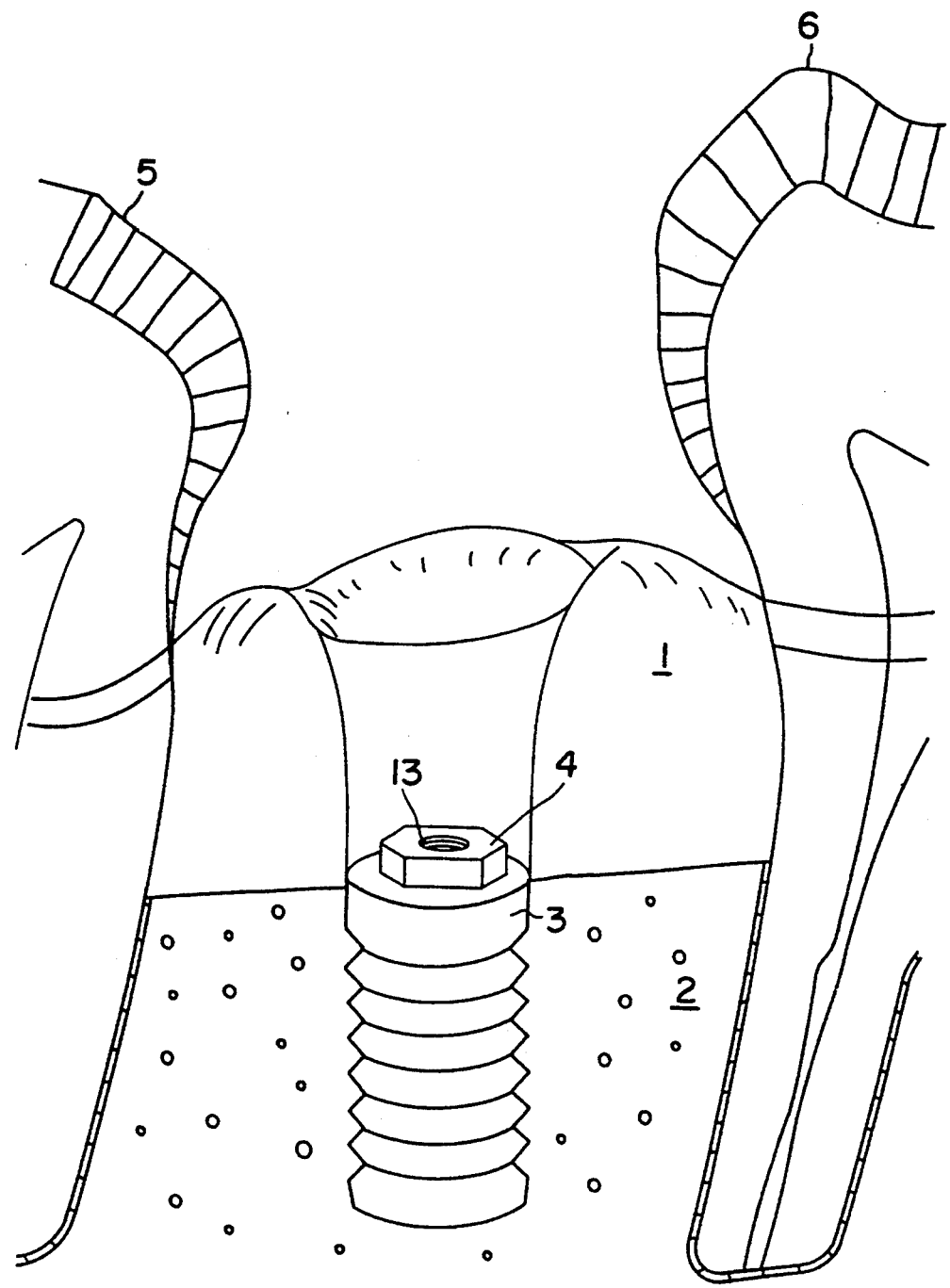
FIG. 1 is a partial cross-sectional view of an implant body anchored in the jawbone.

FIG. 1 shows the first step in the process of making a tooth reconstruction. The gingiva 1 is prepared surgically between two healthy teeth 5, 6 sufficiently to allow the anchoring of an implant body 3 in the jawbone 2. This implant body 3 has an implant head or socket 4 secured at its gingival end, which serves as an aid to positioning and in this case has the shape of a hexagon. Obviously, other shapes can be used for the same purpose. It will always be necessary, however, to ensure that the degrees of freedom between patrix and matrix are kept to a minimum. The socket 4 serves as an anchoring arrangement for an abutment 7, as shown in the following figures. The implant head 4 has a screw thread 13, for receiving a detachable connection. Obviously, other connection arrangements can also be envisaged. Care must be taken to ensure that the detachable connection will not work loose on its own.

Figure 2:
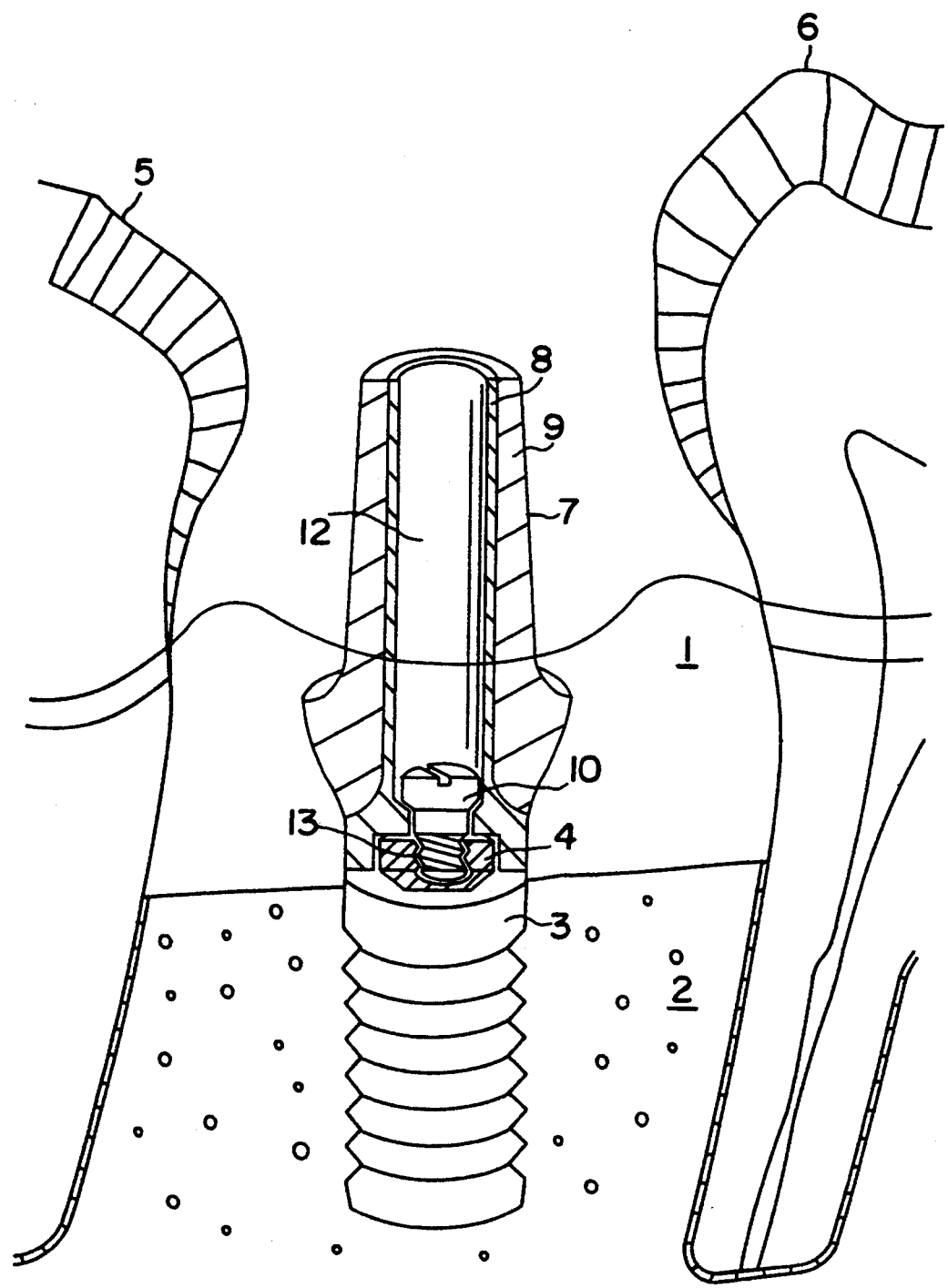
FIG. 2 is a cross-sectional view showing an abutment anchored in the implant, the abutment having a metal core with a sheathing of ceramic, synthetic or composite material.
Figure 4:
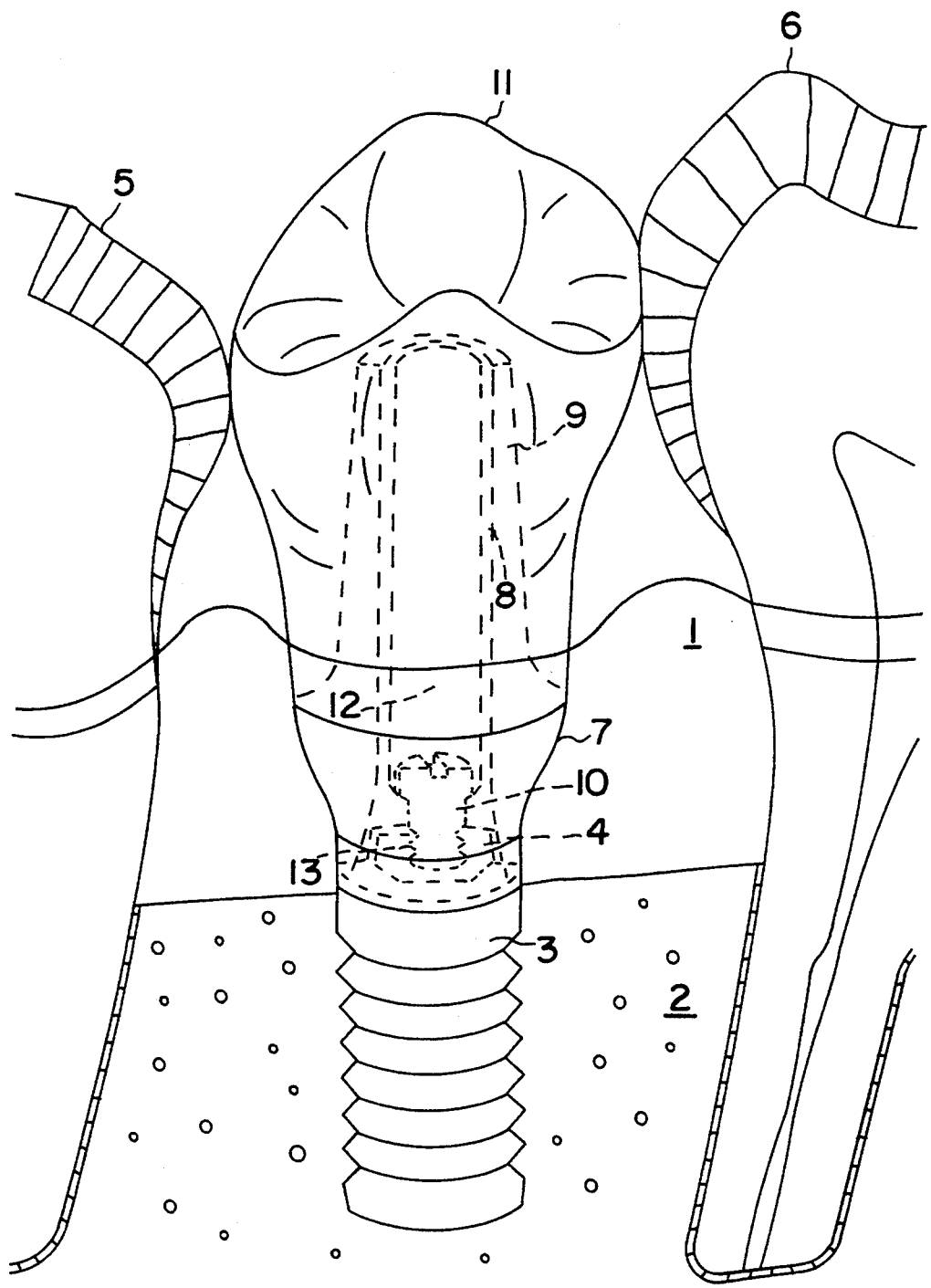
FIG. 4 is a partial cross-sectional view of a reconstructed tooth according to another embodiment of the present invention.

Once healing has occurred following the insertion of the implant body, the abutment 7 may be fitted to the implant body as shown in FIG. 2. The abutment 7 is fashioned as a retention shape and has a metal core 8 with a material sheathing 9 of ceramic, synthetic or composite material. The hollow core 8 has a central aperture 12. As is clearly evident from FIG. 2, the sheathing 9 reaches deep into the gingiva, i.e., approaching the area of the jawbone, as seen in FIG. 4, which shows the sheath attached around the bottom portion of the core and extending an entire distance between a bottom end of a tooth 11 and a bottom end of the abutment 7. If subsequently, in the course of time, gingival recession occurs, at most a region of the tooth-colored sheathing 9 of the abutment 7 will be exposed which will not cause any cosmetic impairment. The retention shape of the abutment 7 can be prepared individually, i.e., any inclined (skew) plane that is required on the implant surface can be fashioned. In this way, optimal shape and attitude can be achieved in the tooth reconstruction.

As FIG. 2 further shows, the connection between the implant body 3 and the abutment 7 takes place exclusively in the metallic region of the two connecting pieces. A screw 10 is passed via the vertical aperture 12 in the abutment 7 and screwed tight from above in the implant head 4. It is evident that the connection must not become unscrewed too easily on its own. All necessary precautions known to the state of the art should be used to ensure that the joint between the implant body 3 and the abutment 7 can be unscrewed only by the use of special means. The positioning between the implant 3 and abutment 7 is carried out by the hexagonal recess at the lower end of the abutment 7 and the hexagonal shape of the implant head 4. The degrees of freedom between the head 4 and the abutment 7 must be kept as small as possible, on the one hand to maintain the predetermined position of the reconstruction and on the other hand to achieve support for the static connection. As already mentioned, other arrangements can also be envisaged withregard to positioning as well as coupling of the head 4 to the abutment 7, as long as the predetermined and defined purpose is still achieved.

In a modified form of the invention, the abutment 7 itself may take the form of the reconstructed tooth, including the aperture 12, which is also present in this case, and which serves invariably for anchoring the abutment 7 to the implant head 4. The aperture 12 is closed, when the reconstruction is finished, at the open end with a plug-like insert of the same material as the abutment 7.

Figure 3:
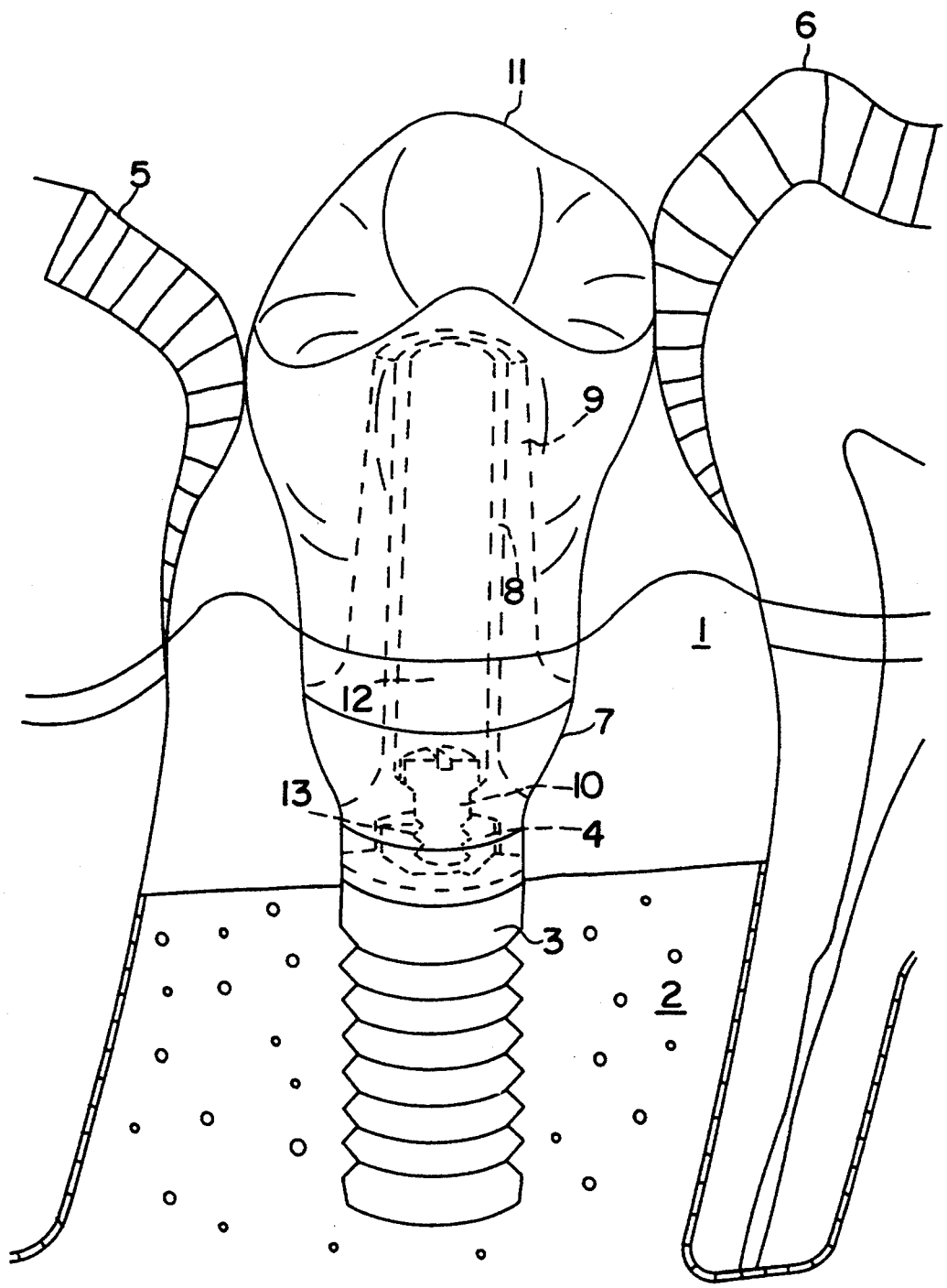
FIG. 3 is a partial cross-sectional view of a reconstructed tooth in accordance with this invention.

FIG. 3 now shows the final reconstruction, which is concluded by placing on a tooth crown 11. When comparing two existing healthy teeth 5, 6 and a reconstructed tooth 11, FIG. 3 itself clearly indicates the manifold possibilities that the described concept can open up and the maximal quality assurance that can thereby by achieved.

A device for the reconstruction of missing or lost teeth thus includes the implant body 3, and means, such as an external thread on the body, for anchoring the body in a jawbone, and the implant head or socket 4 on the body. The device further includes the abutment 7. Means, such as the screw 10 and the screw thread 13 in the implant body 4, is provided for securing the abutment to the body, the abutment being non-rotatable relative to the implant head. The device also includes the detachable prosthesis tooth 11 having a base and a cavity.

The abutment 7 includes the tubular portion 8 which is received in the cavity in the tooth. The tubular portion 8 is substantially the same height as a central portion of the tooth. The abutment 7 has the sheath 9 formed on or attached to an exterior of the tubular portion 8, the sheath forming an abutment face spaced from the securing means 10 and 13. The tubular portion 8 preferably has a narrow cylindrical upper portion, an enlarged bottom portion, and a curved transition cuff between a tubular portion and the bottom portion.

The sheath 9 is attached around the cylindrical portion and the transition cuff. The size of an exposed portion of the sheath 9 below the abutment face is larger than an exposed portion of the tubular portion 8 below the abutment face. Put another way, the bottom end of the tooth 11 is spaced from the transition cuff, and a distance between the bottom end of the tooth and the transition cuff is greater than a distance between the transition cuff and a bottom end of the abutment. The detachable tooth cavity has a length corresponding to the length of the tubular portion 8, and the base of the detachable tooth engages the abutment face.

Although a preferred embodiment of this invention has been illustrated and described herein, it is recognized that changes and variations may be made without departing from the invention as set forth in the claims.

What is claimed is:

1. A device for the reconstruction of missing or lost teeth, comprising:
    an implant body;
    means for anchoring the body in a jawbone;
    an implant head on the body;
    an abutment;
    means for securing the abutment to the body, the abutment being non-rotatable relative to the implant head;
    a detachable prosthesis tooth having a base and a cavity; and
    the abutment including a tubular portion received in the cavity in the tooth, the tubular portion being substantially the same height as a central portion of the tooth, the abutment having a sheath formed on an exterior of the tubular portion, the sheath forming an abutment face spaced from the securing means, a size of an exposed portion of the sheath below the abutment face being larger than an exposed portion of the tubular portion below the abutment face, the detachable tooth cavity having a length corresponding to the length of the tubular portion, the base of the detachable tooth engaging the abutment face.

2. The device as claimed in claim 1, wherein the abutment, as a retention form of the tooth being reconstructed, is made individually for a patient.

3. The device as claimed in claim 1, wherein the abutment includes a metallic material.

4. The device as claimed in claim 1, wherein the abutment includes a ceramic material.

5. The device as claimed in claim 1, wherein the abutment includes a non-metallic material.

6. The device as claimed in claim 1, wherein the sheath is formed of a tooth-colored material.

7. A device for the reconstruction of a missing or lost tooth, comprising:
an implant body, the implant body including means for anchoring the implant body in a jawbone;
an abutment, the abutment having a core, the core having a narrow cylindrical upper portion, an enlarged bottom portion, and a curved transition cuff between a tubular portion and the bottom portion, and a sheath attached around the cylindrical portion and the transition cuff;
means for non-rotatably anchoring the abutment to a top end of the implant body;
a prosthesis tooth, the tooth having a bottom end and a cavity extending into the tooth from the bottom end for receiving a portion of the abutment, the bottom end of the tooth being spaced from the transition cuff, a distance between the bottom end of the tooth and the transition cuff being greater than a distance between the transition cuff and a bottom end of the abutment; and
means for securing the tooth to the abutment,
wherein the core is metallic.

8. A device as claimed in claim 7, wherein the sheath is ceramic.

9. A device as claimed in claim 7, wherein the sheath is tooth-colored.

10. A device as claimed in claim 7, wherein the sheath is further attached around the bottom portion of the core and extends an entire distance between a bottom end of the tooth and a bottom end of the abutment.

11. A device for the reconstruction of a missing or lost tooth, comprising:
an implant body, the implant body including means for anchoring the implant body in a jawbone;
an abutment, the abutment having a core, the core having a narrow cylindrical upper portion, an enlarged bottom portion, and a curved transition cuff between a tubular portion and the bottom portion, and a sheath attached around the cylindrical portion and the transition cuff;
means for non-rotatably anchoring the abutment to a top end of the implant body;
a prosthesis tooth, the tooth having a bottom end and a cavity extending into the tooth from the bottom end for receiving a portion of the abutment, the bottom end of the tooth being spaced from the transition cuff, a distance between the bottom end of the tooth and the transition cuff being greater than a distance between the transition cuff and a bottom end of the abutment; and
means for securing the tooth to the abutment,
wherein the sheath is further attached around the bottom portion of the core and extends an entire distance between a bottom end of the tooth and a bottom end of the abutment.

12. A device as claimed in claim 11, wherein the sheath is ceramic.

13. A device as claimed in claim 11, wherein the sheath is tooth-colored.

* * * * *